United States Patent
Kwon et al.

(10) Patent No.: US 11,560,596 B2
(45) Date of Patent: Jan. 24, 2023

(54) METHOD FOR EXPECTING AND DIAGNOSING UQCRB-RELATED DISEASE

(71) Applicant: Industry-Academic Cooperation Foundation, Yonsei University, Seoul (KR)

(72) Inventors: Ho Jeong Kwon, Seoul (KR); Jeong Eun Kim, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 16/784,478

(22) Filed: Feb. 7, 2020

(65) Prior Publication Data

US 2020/0255897 A1 Aug. 13, 2020

Related U.S. Application Data

(62) Division of application No. 15/338,612, filed on Oct. 31, 2016, now abandoned.

(30) Foreign Application Priority Data

Nov. 6, 2015 (KR) ........................ 10-2015-0155528

(51) Int. Cl.
*C12Q 1/6883* (2018.01)
*C12Q 1/686* (2018.01)

(52) U.S. Cl.
CPC ........... *C12Q 1/6883* (2013.01); *C12Q 1/686* (2013.01); *C12Q 2600/158* (2013.01); *C12Q 2600/178* (2013.01)

(58) Field of Classification Search
CPC ........ C12Q 2600/178; C12Q 2600/158; C12Q 1/68; C12Q 1/6886; C12N 15/111; C12N 15/113; C12N 2310/141
See application file for complete search history.

(56) References Cited

U.S. PATENT DOCUMENTS

2005/0260639 A1* 11/2005 Nakamura ........... C12Q 1/6886
  435/6.14
2006/0150264 A1* 7/2006 Bahn ..................... C12Q 1/6883
  800/18
2008/0009010 A1* 1/2008 Konradi ............. G01N 33/6896
  435/6.16
2008/0306006 A1* 12/2008 Croce ................ A61K 31/7105
  514/1.1
2009/0143279 A1* 6/2009 Mootha .............. A61K 31/4164
  514/1.1
2009/0324596 A1* 12/2009 Kang ..................... A61K 45/06
  424/138.1
2010/0279292 A1* 11/2010 Marsh ..................... A61P 35/00
  435/6.18
2010/0297652 A1* 11/2010 Shelton ................ C12Q 1/6886
  435/6.1
2011/0229504 A1* 9/2011 Fritsche ............... G01N 33/505
  424/185.1
2013/0281493 A1* 10/2013 Freed-Pastor .......... A61K 31/22
  514/342
2017/0002424 A1* 1/2017 Lozano Castro .... C12Q 1/6886

OTHER PUBLICATIONS

Stadthagen et al., Loss of miR-10a activates Lpo and collaobrates with activated Wnt signaling in inducing intestinal neoplasia in female mice, PLOS Genetics, vol. 9, issue 10, e1003913, pp. 1-12. (Year: 2013).*
Yu et al., MicroRNA-19a targets tissue factor to inhibit colon cancer cells migration and invasion, Molecular and Cellular Biochemistry, vol. 380, pp. 239-247. (Year: 2013).*
Ukomadu et al., p21-dependent inhibition of colon cancer cell growth by mevastatin is independent of inhibition of G1 cyclin-dependent kinases, The Journal of Biological Chemistry, vol. 278, pp. 43586-43594. (Year: 2003).*
Shen et al., Genome-wide aberrant DNA methylation of microRNA host genes in hepatocellular carcinoma, Epigenetics, vol. 7, pp. 1230-1237. (Year: 2012).*
Murakami et al., Comparison of hepatocellular carcinoma miRNA expression profiling as evaluated by next generation sequencing and microarray, PLOS ONE, vol. 9, issue 9, e106314, pp. 1-9. (Year: 2014).*
Li et al., Fatostatin displays high antitumor activity in prostate cancer by blocking SREBP-regulated metabolic pathways and androgen receptor signaling, Molecular Cancer Therapeutics, vol. 13, pp. 855-866. (Year: 2014).*
Li et al., SREBP-1 has a prognostic role and contributes to invasion and metastasis in human hepatocellular carcinoma, International Journal of Molecular Sciences, vol. 15, pp. 7124-7138. (Year: 2014).*
Brusselmans et al., Squalene synthase, a determinant of raft-associated cholesterol and modulator of cancer cell proliferation, The Journal of Biological Chemistry, vol. 282, pp. 18777-18785. (Year: 2007).*
Sui et al., Squalene epoxidase (SQLE) promotes the growth and migration of the hepatocellular carcinoma cells, Tumor Biology, vol. 36, pp. 6173-6179. (Year: 2015).*
Montero et al., Mitochondrial cholesterol contributes to chemotherapy resistance in hepatocellular carcinoma, Cancer Research, vol. 68, pp. 5246-5256. (Year: 2008).*

(Continued)

*Primary Examiner* — Dana H Shin
(74) *Attorney, Agent, or Firm* — Amster, Rothstein & Ebenstein LLP

(57) ABSTRACT

Disclosed is a method for expecting and diagnosing UQCRB-related disease, and more particularly, related to a method for diagnosing a UQCRB-related disease and a cholesterol biosynthesis related disease, as well as expecting risks of post-occurrence of the UQCRB-related disease and the cholesterol biosynthesis related disease, simply by measuring an expression level of miRNA, and a kit and a biomarker composition for the method.

2 Claims, 18 Drawing Sheets

(56) References Cited

OTHER PUBLICATIONS

Chang et al., A mutation in the mitochondrial protein UQCRB promotes angiogenesis through the generation of mitochondrial reactive oxygen species, BBRC, vol. 455, pp. 290-297. (Year: 2014).*

"Affymetrix Probe Set" (online), retrieved from the internet on Apr. 12, 2019 at <https://www.ncbi.nlm.nih.gov/geo/query/acc.cgi?view=data&acc=GPL8786&id=26327&db=GeoDb_blob35>. (Year: 2011).

Duttagupta et al., "Impact of Cellular miRNAs on Circulating miRNA Biomarker Signatures," PLoS One, V. 6, No. 6, e20769. (Year: 2011).

"GSE27256" (online), retrieved from the internet on Apr. 12, 2019 at <https://www.ncbi.nlm.nih.gov/geo/query/acc.cgi?acc=GSE27256>. (Year: 2011).

Giray et al., "Profiles of Serum MicroRNAs; miR-125b-5p and miR223-3p Serve as Novel Biomarkers for HBV-Positive Hepatocellular Carcinoma," Mol. Biol. Rep., vol. 41, Mar. 5, 2014, pp. 4513-4519. (Year: 2014).

"MiRBase—Mature Sequence hsa-miR-10a-5P," Accession No. MIMAT0000253, 2018, retrieved from the internet at <http://wwwmirbase.org/cgi-bin/mature.pl?mature_acc=MIMAT0000253>. (Year: 2018).

Hoppe et al., "Increased Expression of miR-126 and miR-10a Predict Prolonged Relapse-Free Time of Primary Oestrogen Receptor-Positive Breast Cancer Following Tamoxifen Treatment," European Journal of Cancer, vol. 49, No. 17, Aug. 19, 2013, pp. 3598-3608. (Year: 2013).

* cited by examiner

Fig. 3A-3B
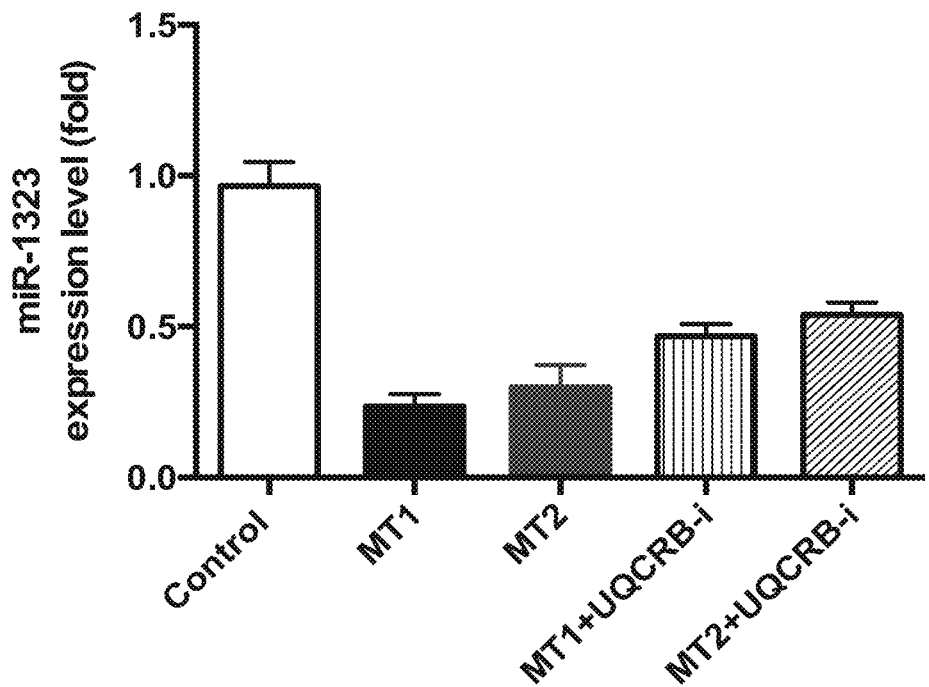
Fig. 3A
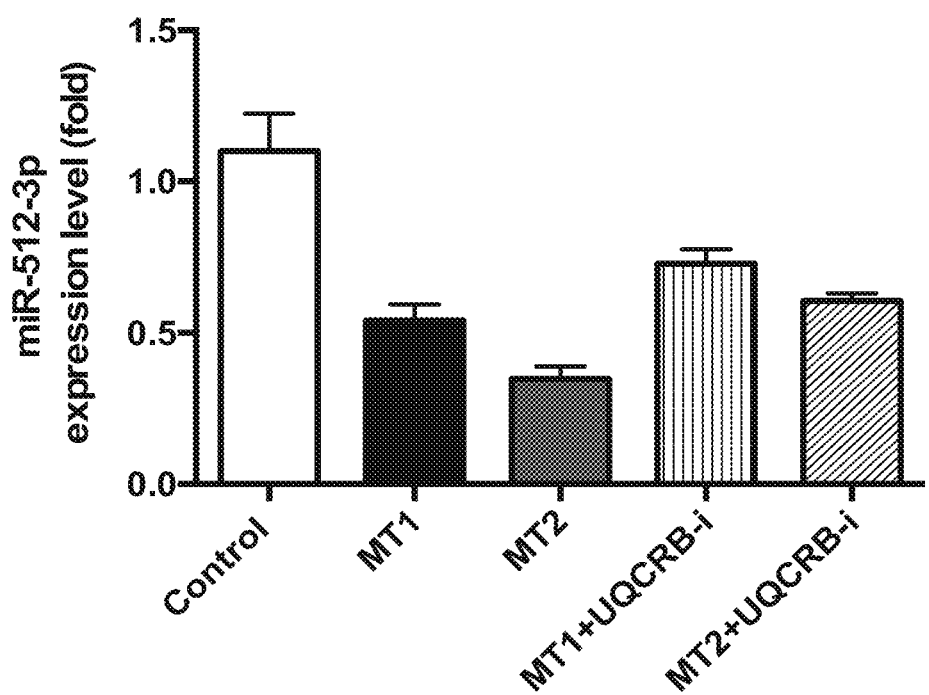
Fig. 3B

Fig. 5

| Term | Count | List Total | Pop Hits | Pop Total | Benjamini |
|---|---|---|---|---|---|
| ● Mutant 1 | Tool: DAVID, Cutoff: Benjamini <0.05 | | | | |
| GO:0016126~sterol biosynthetic process | 10 | 118 | 35 | 13528 | 1.36.E-08 |
| GO:0016125~sterol metabolic process | 12 | 118 | 101 | 13528 | 6.10.E-07 |
| GO:0006695~cholesterol biosynthetic process | 8 | 118 | 26 | 13528 | 6.78.E-07 |
| GO:0006694~steroid biosynthetic process | 11 | 118 | 85 | 13528 | 8.45.E-07 |
| GO:0008203~cholesterol metabolic process | 11 | 118 | 92 | 13528 | 1.48.E-06 |
| GO:0008610~lipid biosynthetic process | 16 | 118 | 323 | 13528 | 2.31.E-05 |
| GO:0008202~steroid metabolic process | 13 | 118 | 202 | 13528 | 2.89.E-05 |
| hsa00100:Steroid biosynthesis | 6 | 55 | 17 | 5085 | 5.72.E-05 |
| GO:0008299~isoprenoid biosynthetic process | 5 | 118 | 20 | 13528 | 3.39.E-03 |
| hsa00900:Terpenoid backbone biosynthesis | 4 | 55 | 15 | 5085 | 2.12.E-02 |
| hsa04010:MAPK signaling pathway | 10 | 55 | 267 | 5085 | 3.92.E-02 |
| hsa01040:Biosynthesis of unsaturated fatty acids | 4 | 55 | 22 | 5085 | 4.48.E-02 |
| ● Mutant 2 | Tool: DAVID, Cutoff: Benjamini <0.05 | | | | |
| GO:0016125~sterol metabolic process | 666 | 15 | 101101 | 13513528 | 5.64.E-06 |
| GO:0008203~cholesterol metabolic process | 6 | 15 | 92 | 13528 | 7.04.E-06 |
| GO:0008202~steroid metabolic process | 6 | 15 | 202 | 13528 | 1.20.E-04 |
| GO:0016126~sterol biosynthetic process | 4 | 15 | 35 | 13528 | 4.01.E-04 |
| GO:0006694~steroid biosynthetic process | 4 | 15 | 85 | 13528 | 4.68.E-03 |
| hsa00900:Terpenoid backbone biosynthesis | 3 | 11 | 15 | 5085 | 6.47.E-03 |
| GO:0008299~isoprenoid biosynthetic process | 3 | 15 | 20 | 13528 | 8.78.E-03 |
| GO:0006695~cholesterol biosynthetic process | 3 | 15 | 26 | 13528 | 1.28.E-02 |
| GO:0006720~isoprenoid metabolic process | 3 | 15 | 44 | 13528 | 3.20.E-02 |

METHOD FOR EXPECTING AND DIAGNOSING UQCRB-RELATED DISEASE

CROSS-REFERENCE TO RELATED APPLICATIONS

This application is a divisional of U.S. patent application Ser. No. 15/338,612, filed Oct. 31, 2016, which claims priority to Korean Patent Application No. 10-2015-0155528 filed Nov. 6, 2015, the contents of each of which are hereby incorporated by reference in their entirety.

BACKGROUND

Embodiments of the inventive concept described herein relate to a method for expecting and diagnosing UQCRB-related disease, and more particularly, relate to a method for diagnosing a UQCRB-related disease and a cholesterol biosynthesis related disease, as well as expecting risks of post-occurrence of the UQCRB-related disease and the cholesterol biosynthesis related disease, simply by measuring an expression level of miRNA, and a kit and a biomarker composition for the method.

Ubiquinol-cytochrome C Reductase Binding Protein (UQCRB), which is one of elements of mitochondria complex III, is known as a target protein of terpestacin that is a low molecular compound inhibiting angiogenesis.

In detail, UQCRB is encoded in a nuclear and is important in fabricating and maintaining mitochondria complex III. Additionally, UQCRB is known as being over-expressed in involved in a liver cancer and a stomach cancer, and involved in several diseases such as hypoclysemia, lactic acid acidosis, and muscle disease.

The inventors, as shown in FIG. 1, has demonstrated that introduction of UQCRB into a cell induces Reactive Oxygen Species (ROS) to be generated in mitochondria and stabilizes HIF-1α to induce angiogenesis (Jung, et al., Mol. Biosyst., 2013).

According to other several reports, complex III of mitochondria respiration chain generates ROS through sensing oxygen in a cell, performing an important function in regulating hypoxia-inducible angiogenesis.

A Hypoxia-Inducible factor (HIF) has been watched in the point that it importantly affects cell survival and initiation of angiogenesis in a hypoxia condition. ROS generated by mitochondria complex III in a hypoxia condition stabilizes HIF-1α protein which is a main regulator of angiogenesis. HIF is formed of a heterodimer complex of HIF-1α and HIF-1β, and especially HIF-1α protein causes initiation of expression of an angiogenesis-friendly factor such as Vascular Endothelial Growth Factor (VEGF).

Micro-RNA (miRNA) is a small untranslated RNA formed of 18~25 nucleotides. Such miRNA is coupled with 3'-Untranslated Region (UTR) to regulate expression of gene (Bartel D P, et al., Cell 116: 281-297, 2004; Lewis B P, et al., Cell 120: 15-20, 2005) and processed from intron, exon, or intergenic region (Rodriguez A, et al., Genome Res 14: 1902-1910, 2004).

The miRNA is involved in various biological processes related to cancer development including proliferation and invasion of cancer cells. Expression of miRNA is known as being regulated bilaterally in many types of cancers (Esquela-Kerscher A, et al., Nat Rev Cancer 6: 259-269, 2006).

However, it has been unknown that miRNA is involved in UQCRB and diseases related to UQCRB.

SUMMARY

Embodiments of the inventive concept provide a new method for diagnosing and expecting UQCRB and a UQCRB-related disease by measuring an expression level of a specific miRNA.

Embodiments of inventive concept provide a biomarker composition for diagnosing and expecting UQCRB and a UQCRB-related disease, and a kit, including the biomarker composition, for diagnosing and expecting UQCRB and a UQCRB-related disease.

According to an aspect of an embodiment, a method for expecting and diagnosing a UQCRB-related disease includes measuring an expression level of at least one miRNA, which is selected from a group formed of hsa-miR-1323, hsa-miR-512-3p, and hsa-miR-10a-5p, in a sample, comparing a pattern of the measured expression level(s) with one of expression levels or several reference patterns; and diagnosing or expecting the UQCRB-related disease from the compared result of the sample and the reference patterns.

In the method, the sample may be selected from a group formed of a blood sample, a serum sample, a plasma sample, a urine sample, and sputum.

In the method, the measuring of the expression level may include measuring an expression level of hsa-miR-1323.

In the method, the measuring of the expression level may include measuring an expression level of hsa-miR-512-3p.

In the method, the measuring of the expression level may include measuring an expression level of hsa-miR-10a-5p.

In embodiments of the inventive concept, an expression level of miRNA may be found by ascertaining a miRNA gene itself, or a miRNA level in which the gene is expressed, that is, an expression level of protein coded with the miRNA gene. A material capable for measuring the level may include a probe or primer specified peculiar to the miRNA gene. In embodiments of the inventive concept, a probe or primer peculiar to the miRNA may be a probe or primer capable of peculiarly amplifying all or a specific region of each of the whole gene of the three miRNA, and the primer or probe may be designed through a method known in the art.

In embodiments of the inventive concept, the primer may mean single strand oligonucleotide capable of acting as an initiation point of template-directed DNA synthesis under a suitable condition (i.e., four different kinds of nucleoside triphosphate and polymerase) in suitable temperature and suitable buffer solution. A suitable length of a primer may be variable in accordance with diverse factors, for example, temperature and use of the primer. Additionally, a primer is unnecessary to have a sequence fully complementary to a partial sequence of a template. It may be enough for a sequence of a primer if it has sufficient complementarity in a range capable of acting the unique function of the primer by hybridization with a template.

Accordingly, a primer according to embodiments of the inventive concept is unnecessary to have a sequence fully complementary to a nucleotide sequence of a gene that is a template, and rather may be enough if it has sufficient complementarity in a range capable of acting its unique function by hybridization with the nucleotide sequence the gene. Additionally, it may be preferred for a primer according to embodiments of the inventive concept to be used in gene amplification.

In the method, the measuring of the expression level may use any way for measuring an expression amount of miRNA, including selecting one from a group formed of reverse transcriptase polymerase chain reaction, real time polymerase chain reaction, Western blot, Northern blot, enzyme linked immunosorbent assay (ELISA), radioimmunoassay (RIA), radioimmunodiffusion, and immunoprecipitation assay.

In embodiments of the inventive concept, the probe may mean natural or modified monomer or linear oligomer of linkages, which may include deoxyribonucleotide and ribonucleotide and may be hybridized peculiarly with a target nucleotide sequence, and indicates a thing that naturally exists or is artificially synthesized. A probe according to embodiments of the inventive concept may be a single strand, preferably, oligodeoxyribonucleotide. A probe according to embodiments of the inventive concept may include natural dNMP (i.e., dAMP, dGMP, dCMP, and dTMP), a nucleotide analogue or derivative. Accordingly, a probe according to embodiments of the inventive concept may also include even ribonucleotide.

In a method for expecting and diagnosing UQCRB-related disease in accordance with embodiments of the inventive concept, protein-level measurement for measuring the expression level may use an antibody. In this case, the marker protein and an antibody peculiar thereto in a biological specimen may form a mixture, that is, an antigen-antibody complex, and an amount of the antigen-antibody complex may be quantitatively measured through a size of a signal of a detection label. This detection label may be selected from a group formed of enzymes, florescent materials, ligands, emitting materials, microparticles, redox molecules, and radioactive isotropes, but may not be restrictive hereto.

In the method for expecting and diagnosing a UQCRB-related disease, the UQCRB-related disease may be related to cholesterol synthesis.

In a method for expecting and diagnosing UQCRB-related disease in accordance with embodiments of the inventive concept, it may be allowable to lower a serum cholesterol level in relation with cholesterol biosynthesis or to raise an LDL or HDL cholesterol. The UQCRB-related disease may be a dyslipidemia, hyperlipidemia, hypercholesterolemia, and microvascular disease and an acute nephritic syndrome which are generated in connection with cholesterol, as well as a kind of cancer such as breast cancer, colorectal cancer, liver cancer, or stroke.

In the method, the UQCRB-related disease may arise from an increase of expression of cholesterol synthetase due to over-expression of UQCRB.

In the method, the cholesterol synthetase may be HMG-CoA reductase (HMGCR), pyrophophosmevalnote decarboxylase (MVD), or lanosterol synthase (LSS).

According to an aspect of an embodiment, a biomarker composition for expecting and diagnosing UQCRB-related disease includes an agent detecting at least one miRNA selected from a group formed of hsa-miR-1323, hsa-miR-512-3p, and hsa-miR-10a-5p.

In embodiments of the inventive concept, an agent for detecting miRNA may mean molecules which can be used in detecting a marker by ascertaining an expression level of miRNA that is the marker whose expression is affected in relation with UQCRB as described above, preferably indicating a probe, primer, or antibody peculiar to the marker. In other words, in the biomarker composition, the agent may be a probe or primer having a sequence complementary to a nucleotide sequence of at least one miRNA selected from a group formed of hsa-miR-1323, hsa-miR-512-3p, and hsa-miR-10a-5p.

According to still another embodiment of the inventive concept, a kit for expecting and diagnosing a UQCRB-related disease includes means configured to measure an expression level of at least one miRNA selected from a group, which is formed of hsa-miR-1323, hsa-miR-512-3p, and hsa-miR-10a-5p, in a sample; and at least one reference pattern including an expression level that is to be compared with the measured expression level of the miRNA that is taken from the sample.

In the case that a kit for expecting and diagnosing UQCRB-related disease in accordance with embodiments of the inventive concept is applied to a PCR amplification process, the kit may selectively include a reagent necessary for PCR amplification, for example, buffer solution, DNA polymerase (e.g., thermostable DNA polymerase obtained from *Thermus aquaticus* (Taq), *Thermus thermophilus* (Tth), *Thermus filiformis, Themis flavus, Thermococcus litoralis*, or *Pyrococcus furiosus* (Pfu)), DNA polymerase associated factor, and dNTPs. In the case that a kit according to embodiments of the inventive concept is applied to immunity analysis, the kit may selectively include a substrate of a label and a secondary antibody. Besides, a kit according to embodiments of the inventive concept may be fabricated to be compartments or a multiplicity of separate packages including the aforementioned specimen component.

The kit may include a primer complementary to at least one miRNA selected from a group formed of hsa-miR-1323, hsa-miR-512-3p, and hsa-miR-10a-5p and configured to amplify the miRNA.

The kit may include an antibody, antisense oligonucleotide, or probe for at least one miRNA selected from a group formed of hsa-miR-1323, hsa-miR-512-3p, and hsa-miR-10a-5p.

BRIEF DESCRIPTION OF THE FIGURES

FIGS. 3A-3C show a result of measuring an expression amount of miRNA through qPCR in accordance with presence or absence of a process with UQCRB-1 (20M), which is a UQCRB inhibitor, in a UQCRB mutant cell strain.

FIG. 5 shows mRNAs significantly upregulated in mutant UQCRB-expressing cells compared to the control.

DETAILED DESCRIPTION

Hereafter, embodiments of the inventive concept will be described in detail. However, the inventive concept may not be restrictive embodiments described below.

<Manufacturing example> Manufacturing Cell Strain

HEK 293, UQCRB mutant cell strains MT1 and MT2, and HepG2 were cultivated in a DMEM medium to which FBS is added. The UQCRB mutant cell strains MT1 and MT2 were prepared according to the method disclosed in the article that had been previously published by the inventor (Chang, et al., Biochem. Biophys. Res. Commun., 2014). PC3, HCT116 were in a RPMI1640 medium to which FBS is added.

<Embodiment 1> Selecting UQCRB-Related miRNA

<Embodiment 1-1> Separating and Sequencing miRNA

For the purpose of processing miRNA, which has different expression patterns in the UQCRB mutant cell strains MT1 and MT2, in comparison with HEK 293 which is used as a control group, total RNA was separated from the UQCRB mutant cell strains MT1 and MT2 and thereafter sequenced.

Total RNA was separated from the HEK 293, the UQCRB mutant cell strains MT1 and MT2, by using a PureLink RNA isolation kit, and the separated total RNA is miRNA-sequenced in Macrogen Inc. to obtain sequencing data.

<Embodiment 1-2> Selecting miRNA Through Comparison of Expression Patterns

Figure 1:
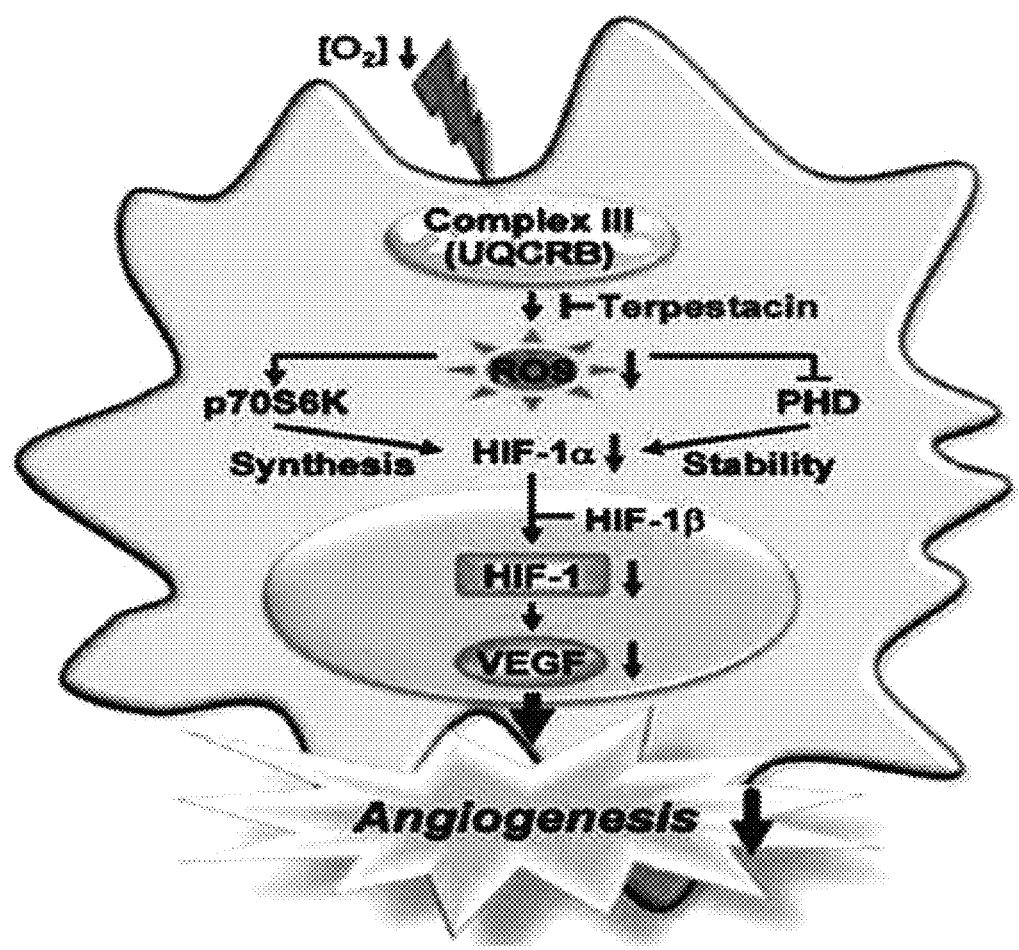
FIG. 1 shows a process that introduction of UQCRB induces generation of ROS in mitochondria and stabilizes HIF-1.alpha. to induce angiogenesis.
Figure 1A:
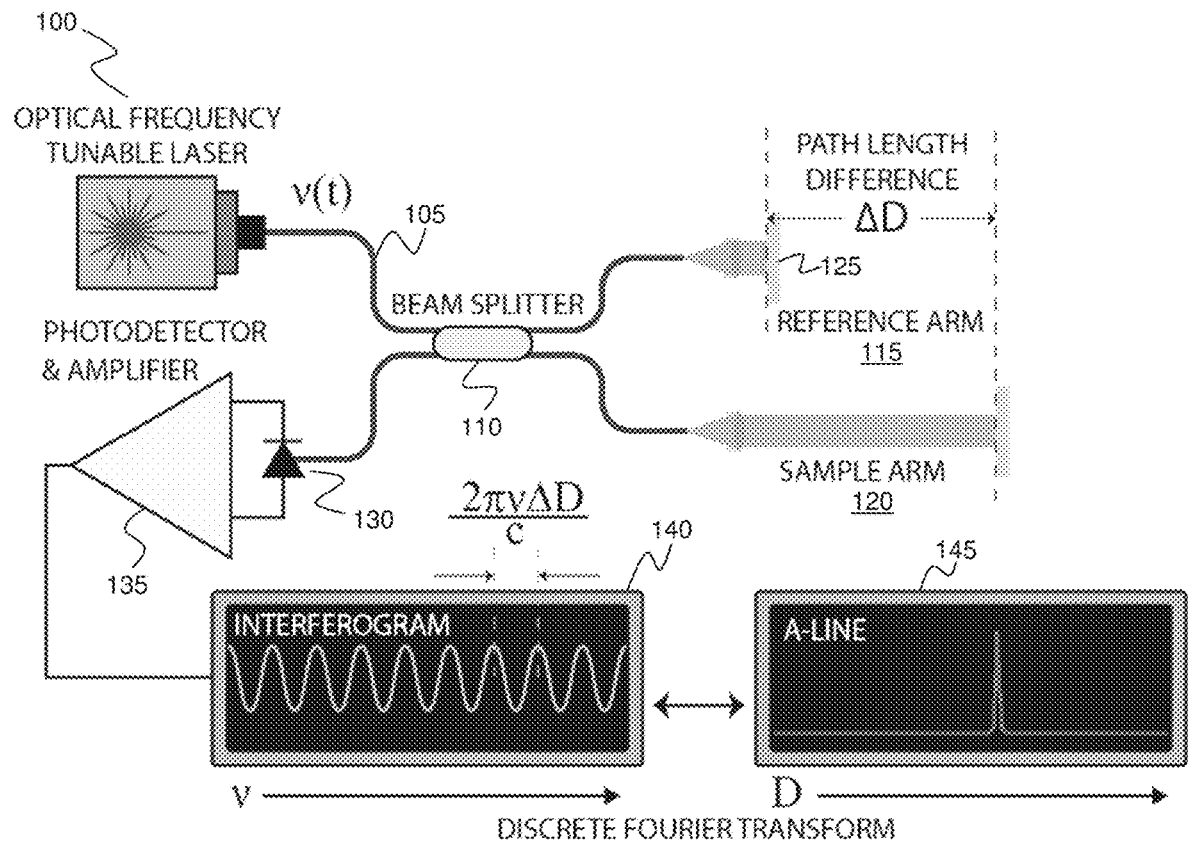
Figure 1B:
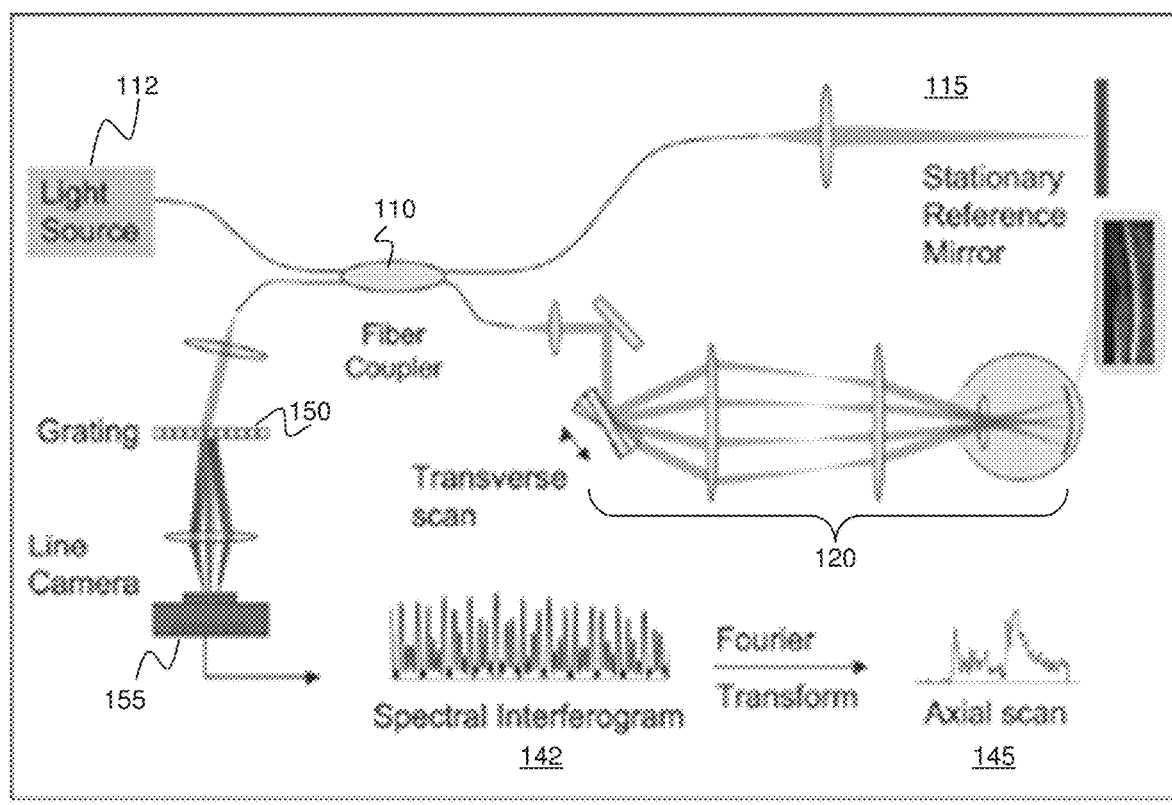
Figure 2:
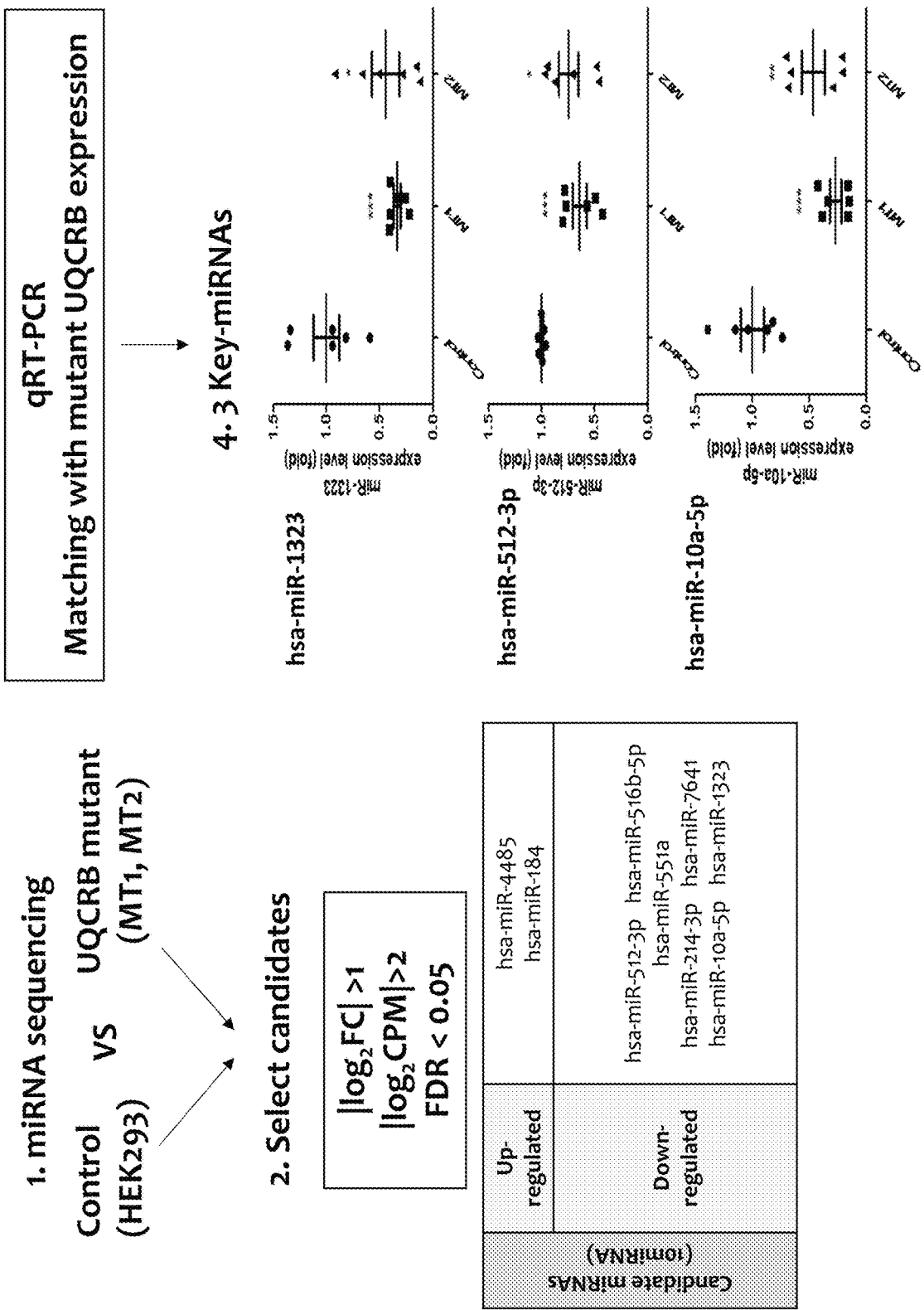
FIG. 2 shows a process of selecting miRNA through comparison of expression patterns in UQCRB mutant cell strains.

As a result of separating total RNA from the UQCRB mutant cell strains MT1 and MT2, 1255 miRNAs were separated and, as shown in FIG. 2, 10 miRNAs satisfying the following three conditions were selected.

|log$_2$ FC|>1, |log$_2$ CPM|>2, FDR<0.05

FC: a difference of expression levels

CPM: the own expression of the factor in each cells.

Expression patterns of the selected 10 miRNAs were manufactured with RT-PCR and three miRNAs of hsa-miR-1323, hsa-miR-512-3p, and hsa-miR-10a-5p were selected in comparison with expression patterns of UQCRB mutant cell strains.

It can be seen from FIG. 2 that the three miRNAs of hsa-miR-1323, hsa-miR-512-3p, and hsa-miR-10a-5p are less expressed in the UQCRB mutant cell strains than in HEK 293 that is a normal cell.

<Embodiment 1-3> Expression Amount of miRNA According Presence or Absence of Processing UQCRB-1 (20M)

For the purpose of ascertaining whether reduction of expression of three miRNAs of hsa-miR-1323, hsa-miR-512-3p, and hsa-miR-10a-5p in the UQCRB mutant cell strains MT1 and MT2 was directly involved in over-expression of UQCRB, UQCRB-1 (20M) as a UQCRB inhibitor was processed in the UQCRB mutant cell strains MT1 and MT2 and an expression amount of miRNA was measured with qPCR.

Figure 3C:
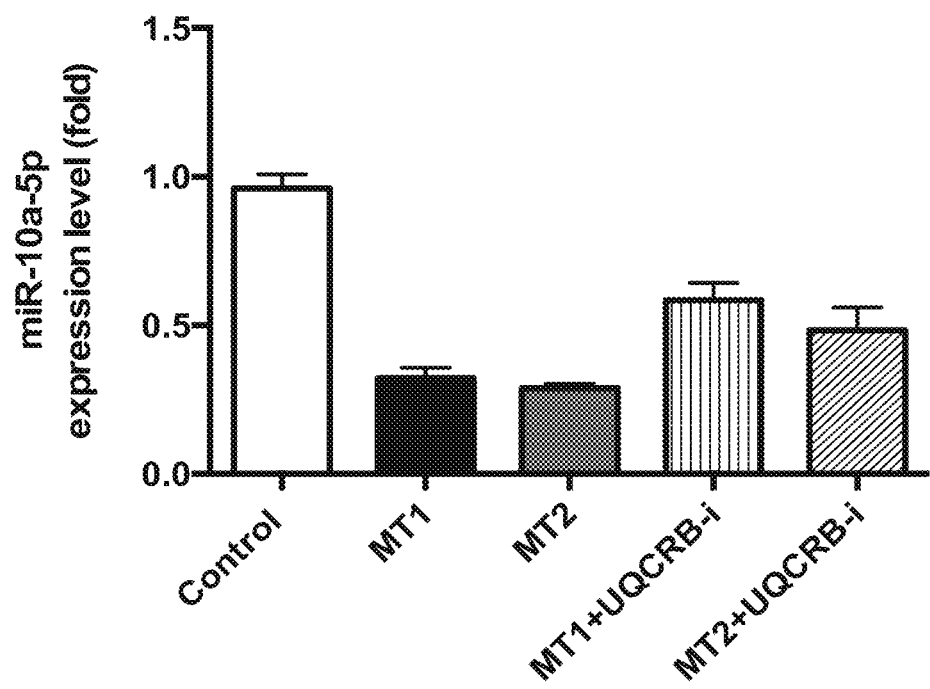

It could be monitored from FIG. 3 that hsa-miR-1323 was restored in 18% of miRNA, hsa-miR-512-3p was restored in 15% of miRNA, and hsa-miR-10a-5p was restored in 24% of miRNA in comparison with HEK293 that was used as a control group when processing a UQCRB inhibitor. This result means that reduction of expression amount of three miRNA is directly involved in over-expression of UQCRB in the UQCRB mutant cell strains MT1 and MT2.

<Embodiment 2> Selecting UQCRB-Related Pathway

<Embodiment 2-1> Separating mRNA and Selecting Cholesterol Metabolic Process

For the purpose of selecting a process in which UQCRB was participated, a process of separating and sequencing mRNA was performed in UQCRB mutant cell strains MT1 and MT2.

Figure 4:
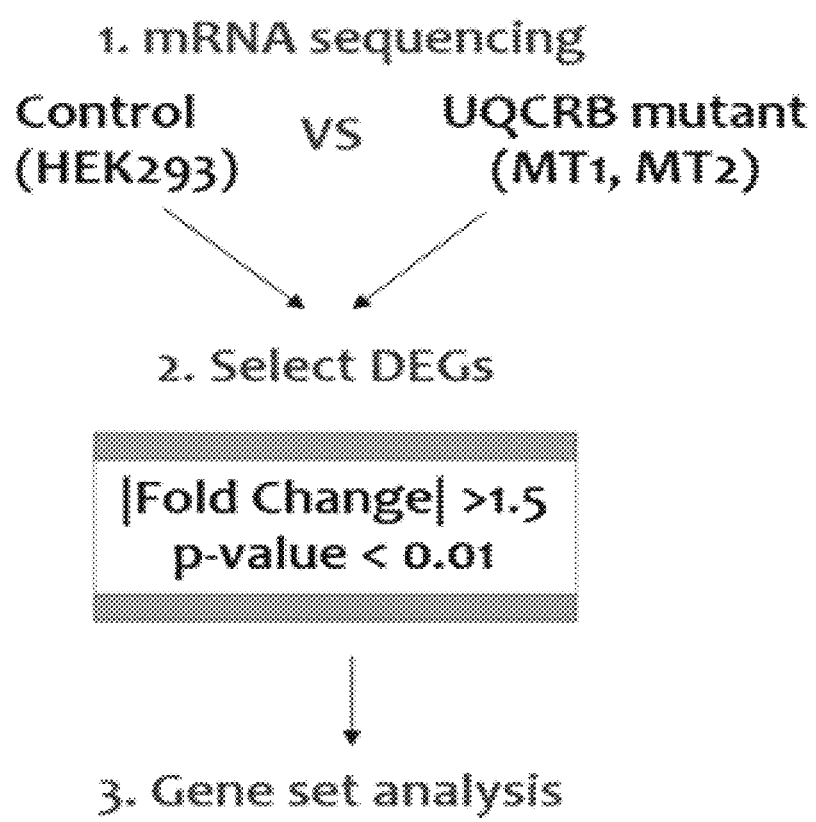
FIG. 4 shows a process of selecting a cholesterol metabolic process.
Figure 6:
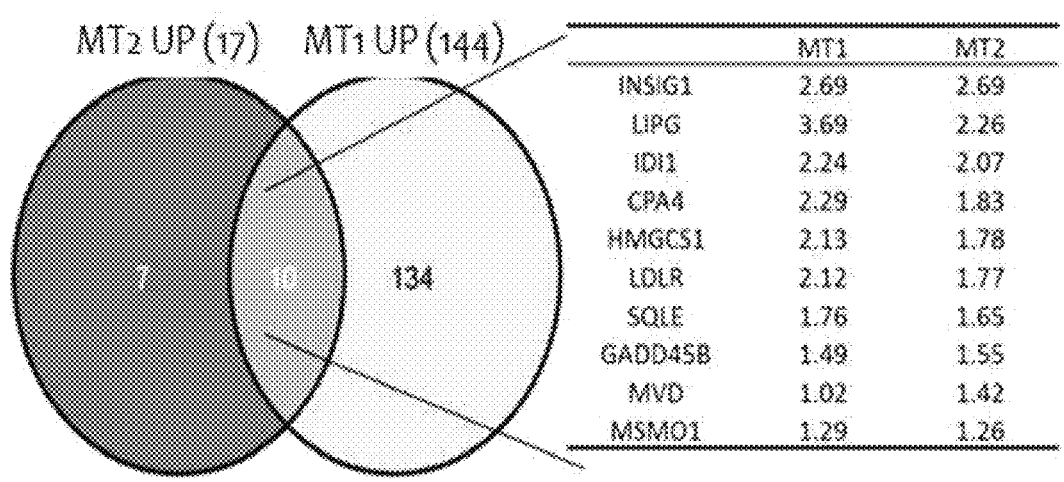
FIG. 6 shows a list of genes upregulated in both of MT1 and MT2 cell lines.
Figure 7:
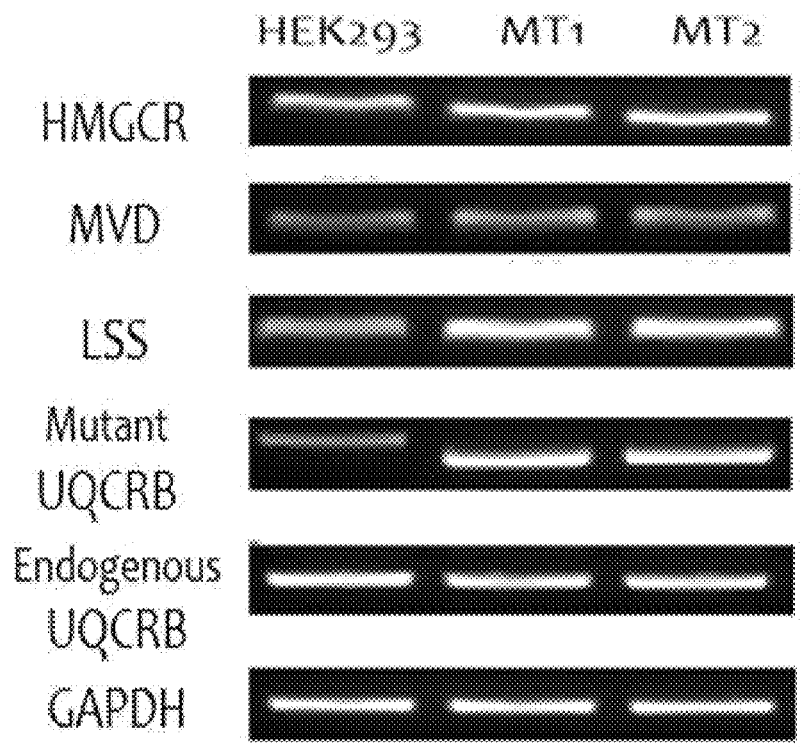
FIG. 7 shows the mRNA expression levels of HMG-CoA reductase (HMGCR), pyrophosphomevalonate decarboxylase (MVD), lanosterol synthase (LSS), mutant UQCRB, and endogenous UQCRB, measured by RT-PCR.
Figure 8:
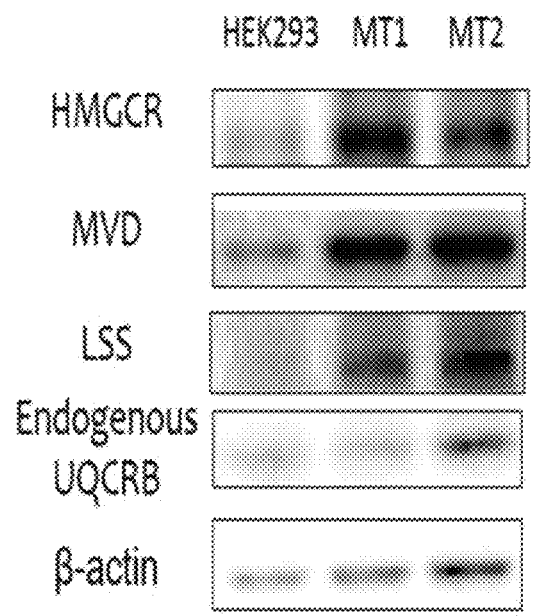
FIG. 8 shows western blot analysis for measuring the protein levels of HMGCR, MVD, LSS and endogenous UQCRB.
Figure 9:
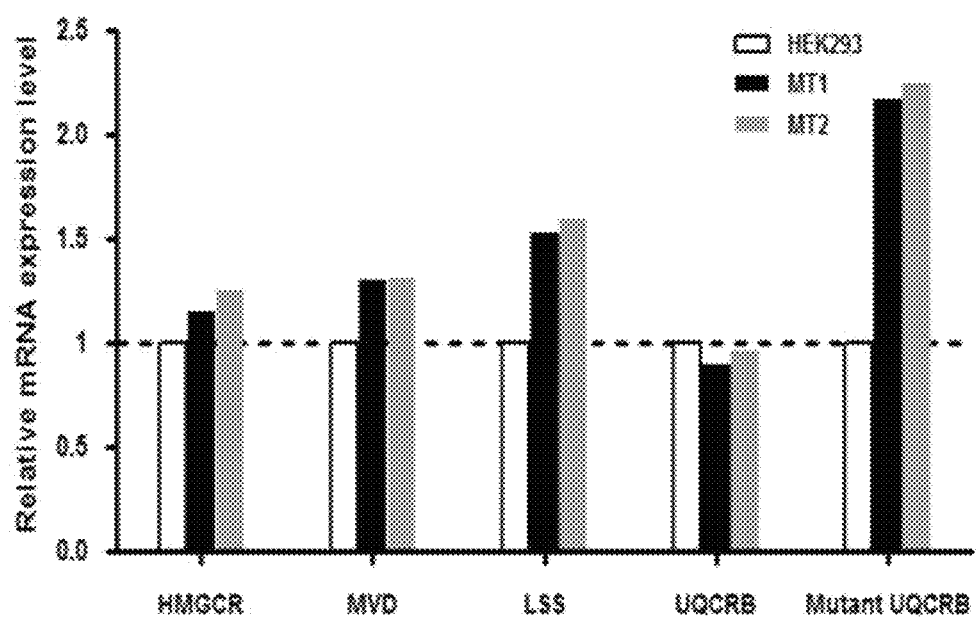
FIG. 9 shows the relative mRNA expression level of 5 genes of FIG. 7.
Figure 10:
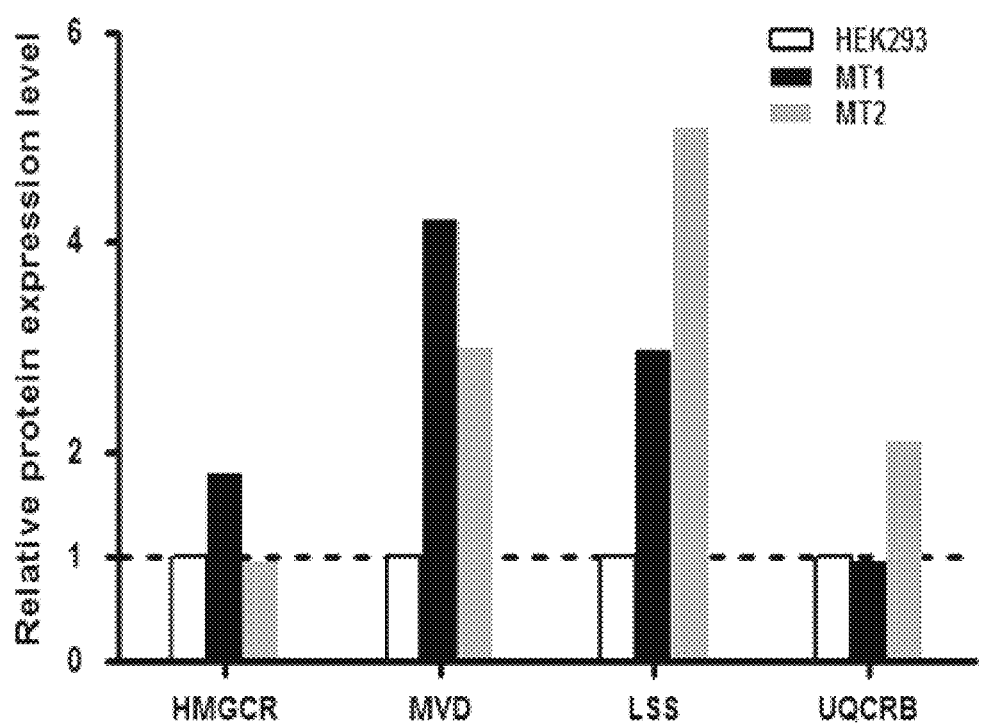
FIG. 10 shows the relative protein expression level of 4 proteins of FIG. 8.

As shown in FIGS. 4 to 6, eight oncology processes (sterol metabolic process, cholesterol metabolic process, steroid metabolic process, sterol biosynthetic process, steroid biosynthetic process, terpenoid backbone biosynthesis, isoprenoid biosynthetic process, and cholesterol biosynthetic process) were over-expressed in UQCRB mutant cell strings MT1 and MT2. The cholesterol biosynthetic process, which was the lowest oncology group, was selected from the eight processes.

<Embodiment 2-2> Verifying Validity for Selection of Cholesterol Metabolic Process For the purpose of verifying validity for selection of cholesterol metabolic process as a pathway in which UQCRB was participated, three enzymes (HMG-CoA reductase (HMGCR), pyrophosphomevalnote decarboxylase (MVD), and lanosterol synthase (LSS)) related to a cholesterol metabolic process were measured in UQCRB mutant cell strains MT1 and MT2 and the result thereof were shown in FIGS. 6 to 9.

Figure 11:
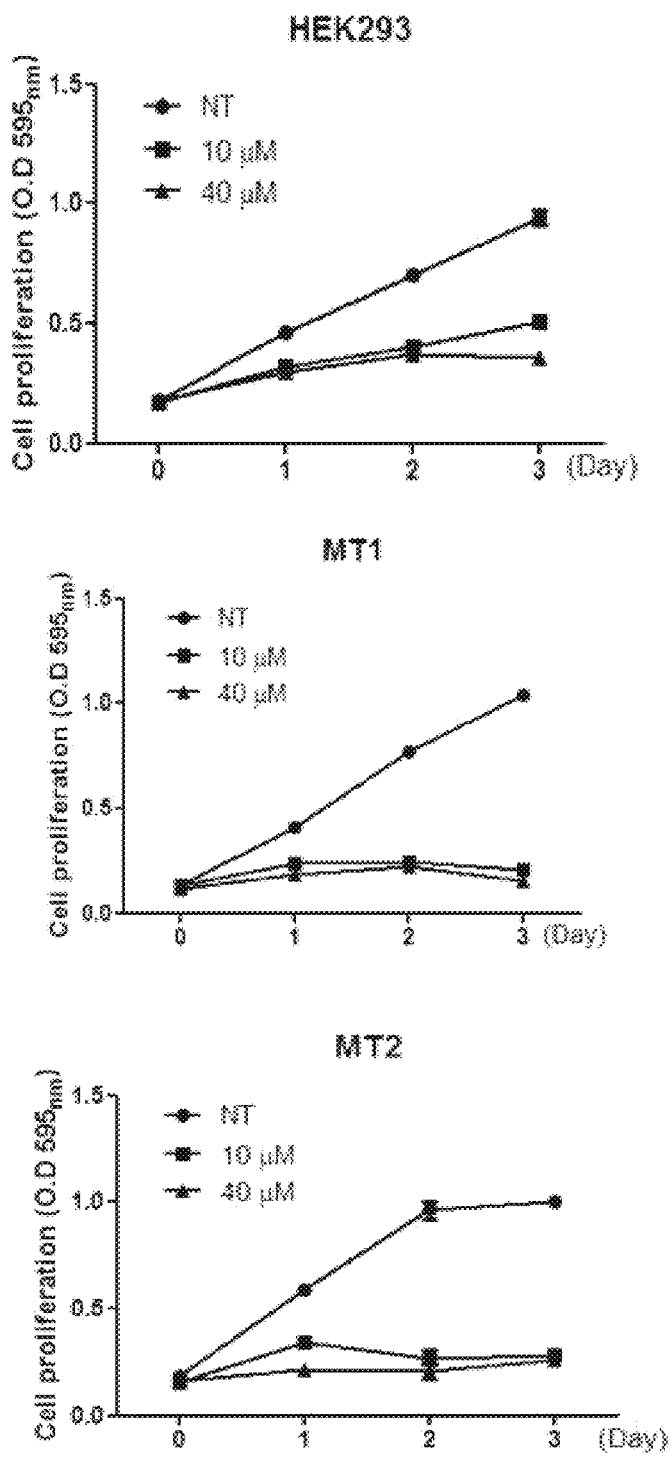
FIG. 11 represents MTT colorimetric assay showing the cell growth of HEK293, MT1, and MT2 cells treated with a cholesterol inhibitor.
Figure 12:
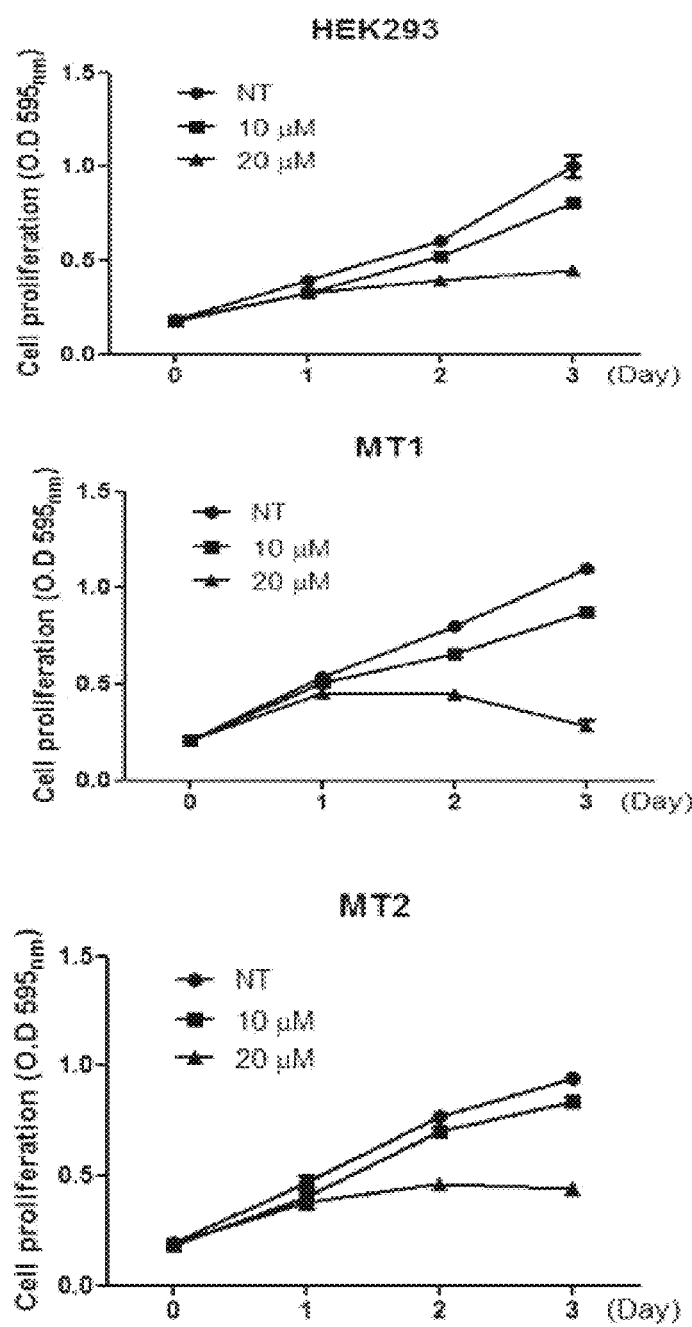
FIG. 12 represents MTT colorimetric assay showing the cell growth of HEK293, MT1, and MT2 cells treated with a cholesterol inhibitor.
Figure 13:
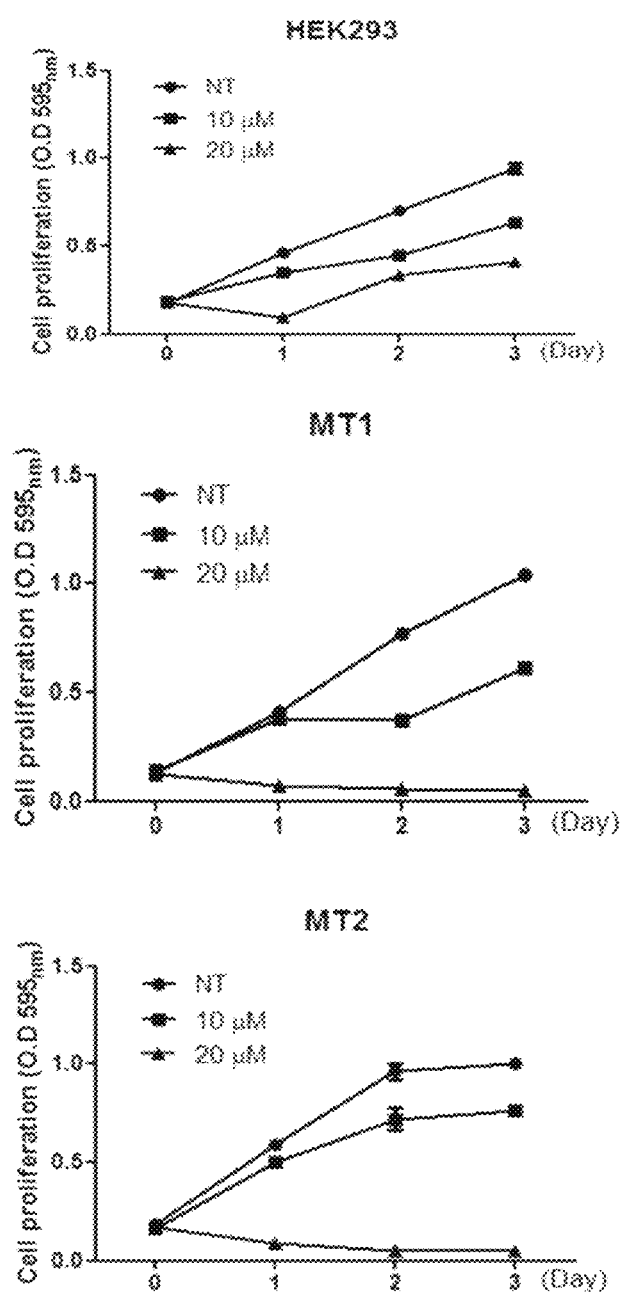
FIG. 13 represents MTT colorimetric assay showing the cell growth of HEK293, MT1, and MT2 cells treated with a cholesterol inhibitor.
Figure 14:
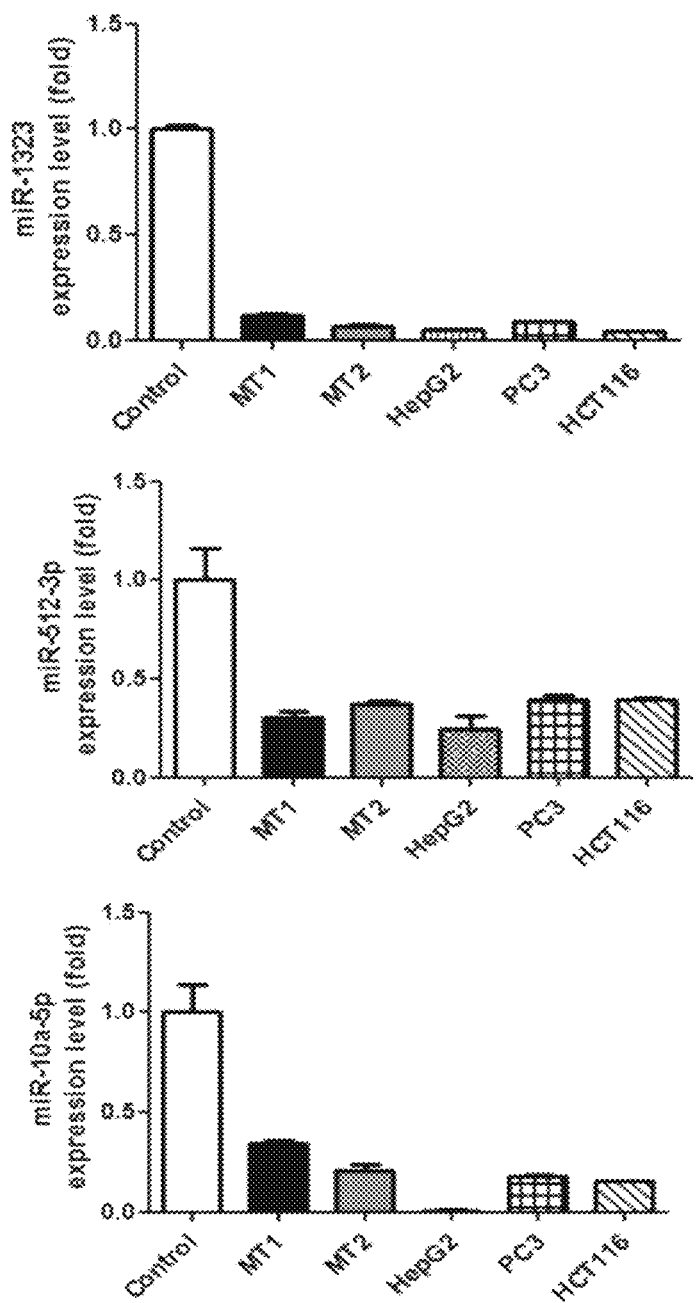
FIG. 14 shows the expression level of miR-1323, miR-512-3p and hsa-miR-10a-5p in control MT1, MT2, HepG2, PC3 and HCT116 cell lines.
Figure 15:
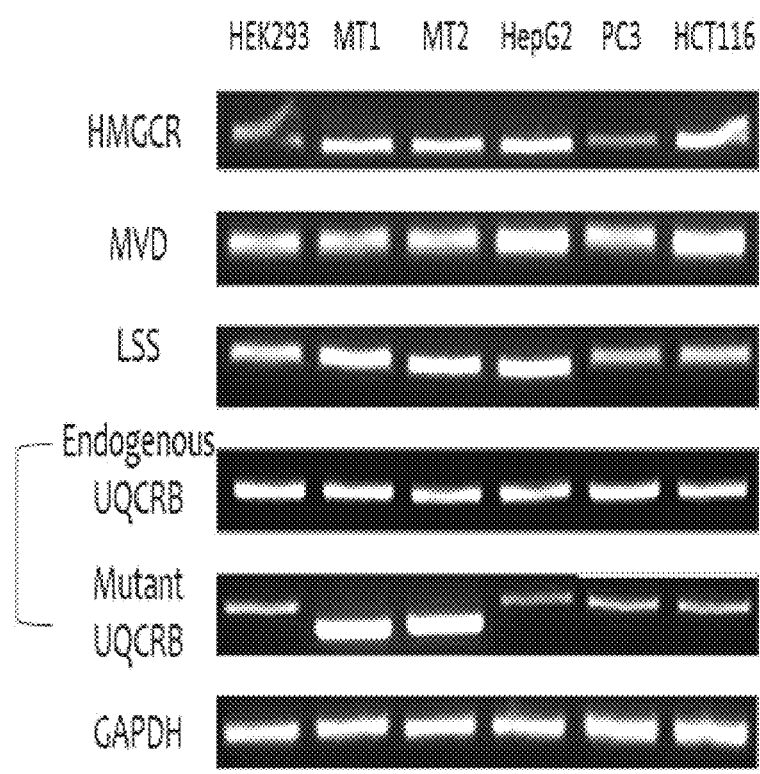
FIG. 15 shows the mRNA expression levels of HMGCR, MVD, LSS, endogenous UQCRB and mutant UQCRB measured by RT-PCR in HEK293, MT1, MT2, HepG2, PC3 and HCT116 cell lines.
Figure 16:
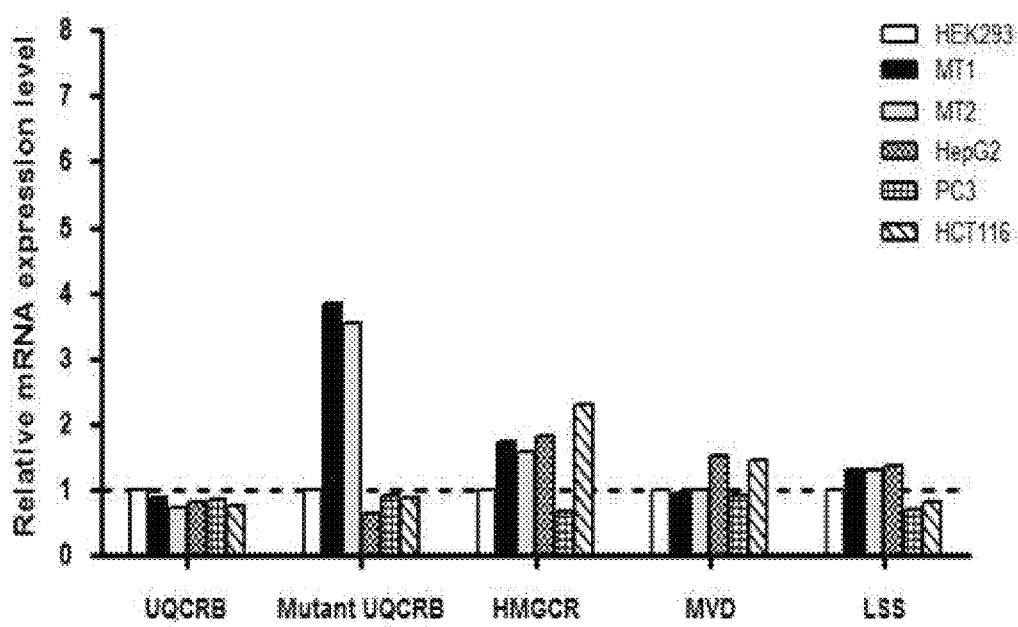
FIG. 16 shows the relative mRNA expression level of 5 genes of FIG. 15.
Figure 17:
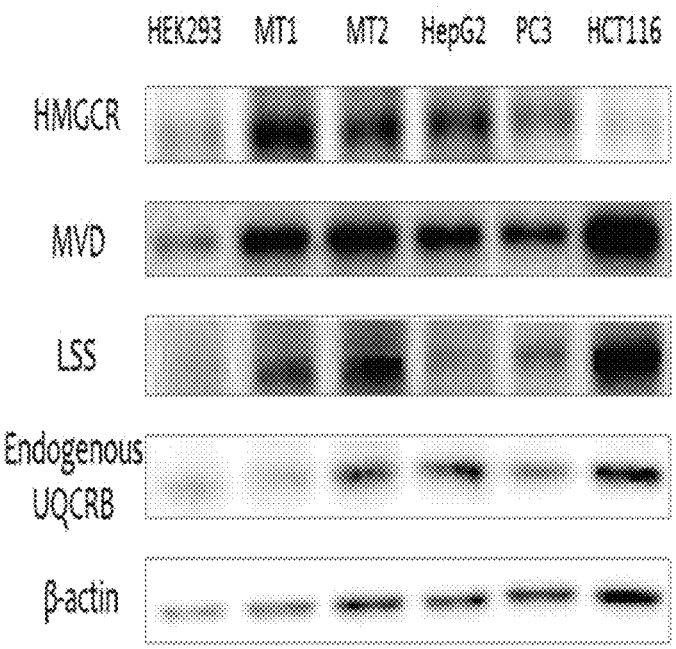
FIG. 17 shows the protein expression levels of HMGCR, MVD, LSS and endogenous UQCRB measured by western blotting.
Figure 18:
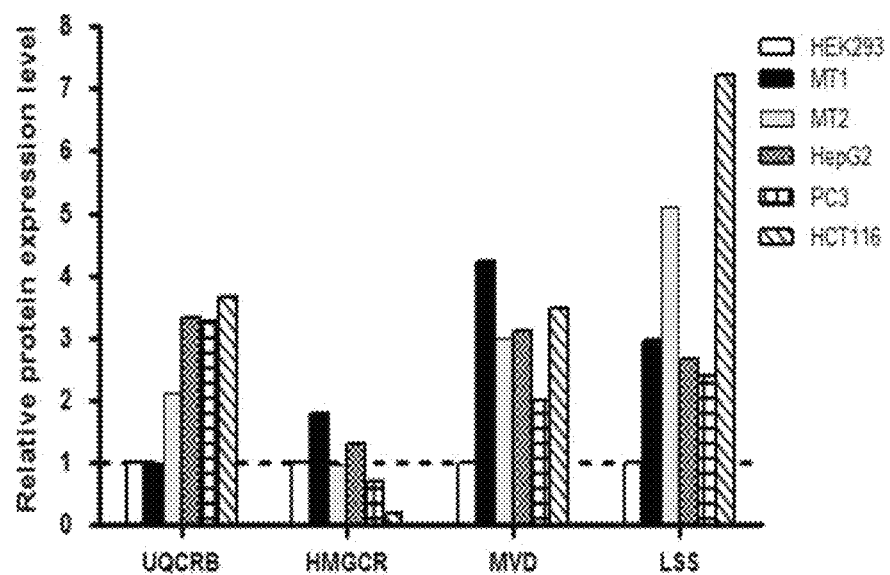
FIG. 18 shows the relative protein expression level of 4 proteins of FIG. 17.

<Embodiment 2-3> Verifying Validity for Selection of Cholesterol Metabolic Process For the purpose of verifying validity for selection of cholesterol metabolic process as a pathway in which UQCRB was participated, a cholesterol synthesis inhibitor was processed in UQCRB mutant cell strains to measure an effect that the cholesterol synthesis inhibitor affects growth of the UQCRB mutant cell strains, and the result thereof was shown in FIGS. 11 to 13.

After processing Fatostatin (sterol regulatory element-binding protein: SREBP inhibitor), Mevastatin (HMG-CoA reductase: HMGCR inhibitor), and YM-53601 (squalene synthase: FDFT1 inhibitor), as cholesterol synthesis inhibitors, in UQCRB mutant cell strains MT1 and MT2, a result of measuring growth rates of the UQCRB mutant cell strains MT1 and MT2 shows that the growth of the UQCRB mutant cell strains MT1 and MT2 are inhibited when processing Fatostatin, Mevastatin, YM-53601 that are cholesterol synthesis inhibitor.

<Embodiment 3> Examining the Relativity of miRNA and Cholesterol Metabolic Process Enzymes Expression levels of three miRNAs of hsa-miR-1323, hsa-miR-512-3p, and hsa-miR-10a-5p, which are selected by Embodiment 1, were measured at the same time with cholesterol metabolic process enzymes in three cancer cell strains which are known as there was over-expressed UQCRB. The results of measuring expression levels are shown in FIGS. 14 to 18.

It can be seen from FIGS. 14 to 18 that as expression amounts of the cholesterol metabolic process enzymes increase in the three cancer cell strains which are known as there is over-expressed UQCRB, whereas expression amounts of the three miRNAs decrease in the three cancer cell strains, the three miRNAs according to embodiments of the inventive concept may be used as a biomarker for diagnosing UQCRB and a disease related to a cholesterol metabolic process involved in UQCRB.

A method according to embodiments of the inventive concept may expect and diagnose a UQCRB-related disease and a disease involved in cholesterol biosynthesis related to UQCRB simply by measuring a specific miRNA expression level.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for treating a Ubiquinol-cytochrome C Reductase Binding Protein (UQCRB)-related liver cancer, the method comprising:
   (i) detecting the UQCRB-related disease by determining that a sample from a subject over-expresses UQCRB protein comprising measuring an expression level of all of hsa-miR-1323, hsa-miR-512-3p and hsa-miR-10a-5p, in a sample from a subject; comparing the measured expression levels with an expression level for said miRs of a HEK293 cell;
   (ii) diagnosing the subject as having a UQCRB-related disease when the sample overexpresses UQCRB protein as indicated by a decrease in the level of all of hsa-miR-1323, hsa-miR-512-3p and hsa-miR-10a-5p relative to expression levels for said miRs of a HEK293 cell determined in step (i); and
   (iii) administering a cholesterol synthesis inhibitor YM-53601 to the subject wherein the UQCRB-related disease has been detected in step (ii).

2. The method of claim 1, wherein the measuring of the expression level of all of hsa-miR-1323, hsa-miR-512-3p and hsa-miR-10a-5p is carried out by reverse transcriptase polymerase chain reaction or real time polymerase chain reaction.

* * * * *